United States Patent [19]

Bailey

[11] 4,014,099
[45] Mar. 29, 1977

[54] DENTAL HANDPIECE

[75] Inventor: Ronald L. Bailey, St. Peters, Mo.

[73] Assignee: Young Dental Manufacturing Company, Hazelwood, Mo.

[22] Filed: Jan. 29, 1975

[21] Appl. No.: 544,910

[52] U.S. Cl. .................................................. 32/27
[51] Int. Cl.² ............................................ A61C 1/10
[58] Field of Search ............ 32/26, 27; 279/29, 89, 279/93

[56] References Cited
UNITED STATES PATENTS

| | | | |
|---|---|---|---|
| 2,188,426 | 1/1940 | Blair | 32/27 |
| 2,263,808 | 11/1941 | Hutchinson | 32/27 |
| 2,343,364 | 3/1944 | Bochenek | 279/29 X |
| 2,791,835 | 5/1957 | Staunt | 32/27 |

*Primary Examiner*—Robert Peshock
*Attorney, Agent, or Firm*—Rogers, Eilers & Howell

[57] ABSTRACT

A dental hand piece including a closed top housing, a bur tube therein which consists of an integral gear and sleeve, the sleeve having an inwardly-projecting boss to engage a bur and drive it, a resiliently releasable member to hold the bur in the tube against accidental displacement, and a positive retaining member to prevent removal of the tool during operation, so that a dental tool can, by insertion into the tube, and by the rotation of the bur tube, be rotated and also secured in the tube.

18 Claims, 6 Drawing Figures

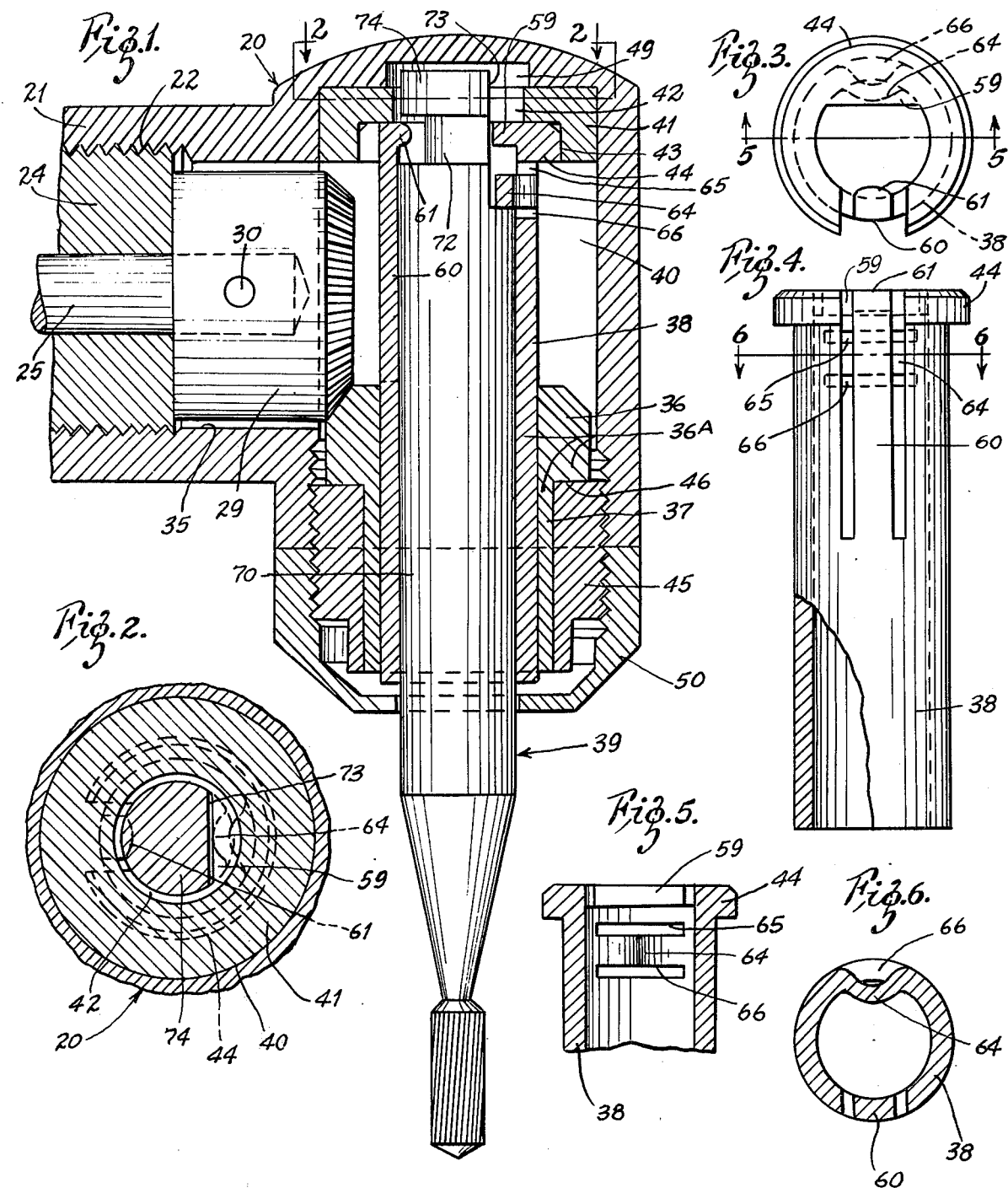

DENTAL HANDPIECE

BACKGROUND OF THE INVENTION:

1. Field of the Invention:

This invention related to improvements in attachment devices used to secure dental tools in dental hand pieces. The invention is more particularly concerned with, but not limited to, means for securing the dental tool within the dental bur tube, whereby part of the dental tool and part of the bur tube interlock so that the dental tool is unable to travel up or down the bur tube, but can be driven by the rotation of the bur tube.

2. Description of the Prior Art:

Many dental instruments incorporating cutting elements as well as sand-paper discs, abrasive wheels, etc., are driven by what is called a latch-type mandrel or bur tube arrangement. This incorporates a tool having a short longitudinal flat at the end of a shank, the shank also having a circumferential groove. Historically the tool or instrument has been driven by a rotating bur tube which has a chordal hole broached into the end to receive the flat of the bur shank for obtaining the rotational drive, and either a hinged latch or sliding latch operated from outside the end of the hand piece, to be slipped into the groove formed in the mandrel to engage the mandrel so that it does not come out of the handpiece.

The present invention has advantages over that type arrangement. It has no latch and so can have a smaller head of the handpiece, whence it is easier to reach the buccal or outside surfaces of the teeth with less distention of the cheek. It also eliminates the necessity of having openings in the back part of the instrument head where bacteria and saliva can enter the hand-piece, making it more aseptic. It eliminates use of the latch as the thrust bearing for the mandrel, and consequently eliminates a factor causing rapid wear and that creates a possible safety hazard, in that, once the latch wears sufficiently, the mandrel and/or dentral instrument can fall out of the handpiece. The present invention also eliminates use of a latch as a stationary member in the handpiece in which the mandrel rotates, and hence reduces heat and friction. It reduces end play that is due to the design of the latch-to-groove attachment that reduces efficiency and accuracy. And by eliminating a slotting operation, and a drilling and tapping operation to hold the screw for the latch, plus the latch and other parts, a reduction in cost is obtained.

The present invention can use the conventional bur or tool shank with the flat and groove, but drives by a fixed radially-inward projection that engages the flat after a short arcuate movement of the bur tube relative to the bur shank, such movement also causing the overhanging flat lug of the bur tube to move into the groove under the flange of the bur shank to prevent the bur from coming out of the tube. Also a spring latch operates toward the same and releasably retains the bur shaft when the bur does not have the aforesaid arcuate displacement.

With this construction, the entire latch system is eliminated allowing the design of a much smaller head, the elimination of the mandrel rubbing the latch and elimination of the wear that occurs on the conventional latch mechanism and on the mandrel and/or instrument. There is also no intermediate tube between the dental tool and the bur tube as there are in devices known in the prior art.

Another embodiment of this invention is that the contra angle back end portion of this handpiece will allow the dentist to use not only the latch type head but the friction grip head and the triple seal prophylaxis head giving him complete flexibility and utility for the contra angle back end portion of the handpiece.

Further, the arrangement can be assembled from one end only of the handpiece head. The single restricted opening at the working end of this contra angle significantly lowers the area in which debris, saliva and bacteria can enter the handpiece. Consequently, the handpiece can maintain better asepsis and leak less oil and lubricant than the handpieces now in use.

Another old means used to secure a dental instrument in the handpiece is to use a tube or a slitted collet to grip the dental instrument, wherein a cam-shaped tube which surrounds the collet pushes in the fingers between the slots so that they may grip a dental tool. The disadvantages of this construction, as to cost and difficulty of manufacture, as well as difficulty in properly centering the tool in the collet and excessive wear, are self-evident.

The groove grip used in the present invention eliminates the problems caused by the prior art devices. Because of the design of the present invention, the parts of the device may be more easily machined, so that the problem with eccentricity can be obviated. There is also negligible difficulty with the breaking of any part of the present invention.

Also, the present invention can be assembled from the instrument end only. In this assembly, thrust bearings can be set in properly adjusted position, and locked; and the journal bearings are arranged to promote maximum stability against tool wobble.

DESCRIPTION OF THE DRAWINGS:

FIG. 1 is a central vertical sectional view of the head of an angle dental handpiece illustrated in accordance with the invention, with a dental bur being shown inserted and retained, and in position to be driven by the rotation of the bur tube;

FIG. 2 is a top sectional view of the head of the handpiece taken on the line 2—2 in FIG. 1;

FIG. 3 is a top view of the dental bur tube;

FIG. 4 is a side view of the bur tube with a lower section being shown broken away;

FIG. 5 is a side sectional view of the top portion of the bur tube taken on the line 5—5 in FIG. 3; and FIG. 6 is a top sectional view of the bur tube taken on the line 6—6 in FIG. 4.

DESCRIPTION OF THE PREFERRED EMBODIMENT:

Referring to FIG. 1, a housing 20 that constitutes the head of the handpiece is provided with a lateral tubular extension 21, internally threaded at 22 so as to receive the externally threaded bearing sleeve 24. The bearing sleeve 24 is adapted to support a drive shaft 25 which extends through the sleeve 24 to a position so that it may be connected to a bevel gear 29 by a pin attachment 30, which may be pressed into place. The bearing sleeve 24 is adapted to confine the gear 29 in the housing 21 and to adjust its position relative to a companion gear to be described. The drive shaft 25 is driven by a motor usually with a flexible shaft connection (not shown).

The housing tubular extension member 21 is provided with a bore 35 of great enough size to allow clearance of the gear 29. The teeth of the gear 29 mesh with the teeth of a gear 36. The gear 36 is formed on an outer sleeve 37 that is secured to the outside of a bur tube 38 so as to be integral therewith, thus comprising the bur tube assembly 36A, with the rotation of the gear 36 driving the bur tube 38. The bur tube 38, in turn, is adapted to receive the shank of a bur or other dental instrument 39.

The bur tube 38 and the gear 36 secured integrally thereto, are rotatably supported in the bore 40 in the head 20. At the top of the head 20, the bore 40 receives a bushing 41 which can be soldered into place. The bushing 41 has a cylindrical bore 42 and a downwardly facing circular recess 43. This recess acts as a bearing for the cylindrical flange 44 on the upper end of the bur tube 38. Above the bushing bore 42, there is a cylindrical counterbore 49 in the upper end of the housing 20, in which the top end of the bur 39 may be received and may rotate. There is also a bearing sleeve or lower bushing 45 for the bur tube subassembly threaded into the lower end of the housing 20, to rotatably receive the lower end of the bur tube assembly 36A. The two axially spaced bushings 41 and 45 provide stable support for the tube 38.

The threads on the sleeve 45 home on threads in the lower part of the housing 20. When the threads are properly interengaged, the upper end of the sleeve 45 engages a shoulder 46 of the gear 36 to displace it and the bur tube upwardly in such a way that the gear 36 will properly mesh with the gear 29, and also so that the bur tube 38 will rest with its upper end having a proper thrust bearing fit within the bore 43 of the bushing 41. A cap 50 has interior threads that also engage with the bearing sleeve threads so that the cap 50 fits on the lower part of the housing 20. The cap 50 has a cylindrical opening at its bottom. When the cap 50 is drawn tightly onto the threads, it acts also as a lock-nut for the bearing sleeve 45 in the head 20.

The bur tube 38 is a hollow rod which can have a circular shape as illustrated in FIG. 1 through FIG. 6, but may also be noncircular in shape. The bur tube 38 has a bore of size to allow a dental instrument, such as dental bur 39, to snugly fit within it, but yet to be readily removed by hand. At the top of the bur tube 38, a head or flange 44 has a lug 59 which may be flat, that overhangs one side of the upper internal surface of the bur tube 38. Opposite the lug 59 there is also a latch device, which consists of a section 60 upstanding between two longitucinal slots through the wall of the bur tube 38. At the top of this latch 60 there is a rounded detent projection 61 which extends inwardly toward the center of the bur tube. The latch tongue 60 acts as a spring.

On the side of the bur tube 38 in a position opposite the latch 60 and just below the flange 44, there is an indentation or drive key 64 which projects inwardly from the wall of the bur tube 38 toward its center. This indentation or drive key 64 is struck inwardly from between two circumferential slots 65 and 66.

The bur tube 38 is designed to receive a rotary dental instrument, such as a dental bur 39. The bur 39 conventionally has a shank 70 having a circumferential groove or neck 72, leaving a top flanged head 74 above the groove 72. The bur also has a recession or flat chordal surface 73 extending across the flange 74, the neck or groove 72, and downwardly below the neck, forming a ledge 75 in shank 70.

OPERATION

To assemble the head, the bushing 41 is secured in place. The bur tube assembly 36A is first assembled, as by a press or soldered fit of the bur tube 38 into the gear sleeve 37 so that they are firmly attached together for present purposes. This sub-assembly is inserted into the head 20 from the bottom end until the flange 44 seats in the recess 43 of the bushing 41.

The cap 50 can be pre-fit with the collar 45 by threading the cap 50 on the projected threads of the collar 45 a predetermined distance, with the cap 50 being secured to the collar 45 by an adhering substance, such as a strong epoxy glue. With the cap 50 and the collar 45 secured together, the threaded collar 45 is then placed around the sleeve 37 and threaded into the head so as to engage the shoulder 46 on the gear 36 and urge the sub-assembly 36A up to establish proper thrust bearing fit of the bur tube. The pre-set combination of the collar 45 and the cap 50 is such that the seating of the flange 44 in the recess 43 occurs simultaneously with the contact of the top portion of the cap with the bottom portion of the head. In the foregoing assembly, there are only two parts to be separately attached to the head. Of course, if it is desired, the collar 45 may be separate from the cap 50, and the collar 45 may be threaded into the head first so that the sub-assembly 36A is urged upward to obtain proper thrust bearing fit of the bur tube. Then the cap 50 may be threaded onto the collar 45.

To install a dental tool 39 into the handpiece, its shank 70 is inserted through the cap 50 and the bore of the bur tube 38, wherein it fits smoothly, and the flat 73 is so aligned with the lug 59 on the bur tube 38 as to permit the head 74 to pass through the opening 42 in the bushing 44 until the ledge 75 of the shank 70 engages the bottom of the lug 64 that projects inwardly from the bur tube 38. When this occurs, the flange 74 of the tool 39 extends completely above the flanged end 44 of the bur tube 38. In being inserted, the flange 74 engages the rounded head 60 of the spring latch 61, displaces it, and passes beyond it, permitting the head 60 to snap back under the head 74. The shank head 74 then extends into the cylindrical counterbore 49 of the housing 20, the counterbore 49 having sufficient space to allow the shank head 74 to rotate within it.

In this neutral position, there is enough clearance between the flat surface of the shank chordal indention 73 and the corresponding flat 59 of the bur tube 38 that relative bur tube 38 can have such relative angular movement in relation to shank 70 that the drive lug 64 engages the flat 73 in a manner to cause rotation of the bur tube 38 to rotate the bur 39, when bur tube 38 is rotated by gears 29 and 36. When the drive lug 64 engages the flat 73, there is also enough relative angular displacement of the tool 39 in the bur tube 38 to cause part of the shank head 74 to overlie the lug 59 of the bur tube 38. Such positioning of the shank head 74 above the lug 59 of the bur tube 38 positively prevents the shank 70 from moving downwardly out of the bur tube bore during operation of the instrument, by any downward force exerted on the bur 39. It can also be seen that a fixed part of the bur tube 38 that projects inwardly can have means to slide into the groove 72 of the shank 70 and prevent its downward motion and simultaneously have an element to engage the shank 70. It is preferred to have the drive key 64 and the lug 59 separate as shown, although they may be brought together into one piece having both functions.

When the instrument is subjected to a reverse force, or is otherwise returned to or through a neutral position, the tool cannot fall out even though no part of the head 74 overlies any part of lug 59, because the tool 39 is retained by the spring latch 60. A reverse beyond the neutral position causes a lock-in by movement of the flanged head 74 in a relative angular direction opposite to the normal drive, to again overlie the lug 59.

It can be seen that the present drill is assembled through the opening created by the removal of the cap 50 at the bottom of the housing head 20, there being no openings at the top or in any other point of the housing head 20 which could allow saliva or bacteria to enter the interor of the housing head 20. There are also no slots or other recessions at the bottom of the bur tube 38 which would allow the saliva or bacteria to creep in and be lodged within the housing head 20.

When the various components are assembled as described above, the shank 70 of the dental bur 39 may be removed from the bur tube 38 while the bur tube is stationary, by rotating the bur 39 until no part of the shank head 74 is above the lug 59 of the bur tube 38, and the lug 59 and flat 73 are aligned. The shank 70 may then be removed from the bur tube 38 by pulling the bur 39 with the fingers. In this action, the downward force of the shank head 74 pushes against the rounded latch projection 60 of the spring latch 61 and forces it outwardly to allow movement of the shank head 74 past the projection 60. The bur 39 may then be removed from the bur tube 38 without any further resistance.

Various changes and modifications may be made within this invention as will be readily apparent to those skilled in the art. Such changes and modifications are within the scope and teaching of this invention as defined by the claims appended hereto.

What is claimed is:

1. In a dental handpiece comprising an instrument holder, having a tubular recess to receive a dental instrument with a shaft insertable in the recess the holder having releasable holding means to secure the dental instrument in the recess of the instrument holder to prevent the instrument's removal but releasable to allow removal by a pull of the finger, the hollow also having a drive means for engagement with the instrument to rotate the dental instrument with the instrument holder, and the holder having additional means rendered aperature by operation of the drive means to prevent the removal of the instrument while the instrument holder and instrument are in motion.

2. The structure of claim 1 wherein the dental instrument has a conventional flat, the structure having means to rotate the dental instrument that includes a tube with an inward projection unitary with the tube, with the projection adapted to engage the flat of the dental instrument.

3. The structure of claim 1, wherein the dental instrument has a conventional flat, the structure having means to rotate the dental instrument including a tube with an inward projection unitary with the tube, with the projection being located adjacent a slot in the wall of the tube, the projection being adapted to engage the flat of the dental instrument.

4. The structure of claim 1, the structure having means to rotate the dental instrument that includes a tube with an inward projection unitary with the tube and with the projection adapted to interact with a dental instrument of the type having a recessed vertical portion in the top section of its shank, so that by the interaction the projection drivingly engages this vertical surface of the dental instrument.

5. The structure of claim 1 wherein the dental instrument has a conventional flat, and the instrument holder comprises a tube having means to drive the tube comprising a driven gear unitary with the tube adapted to be connected to and propelled by a drive gear in the handpiece, and the means to rotate the dental instrument comprises an inward projection unitary with the tube located at a position above the driven gear, and the means to allow removal of the instrument holder from the handpiece without displacement of the drive gear in the handpiece comprises an upper portion of the instrument holder located above the driven gear, the upper portion of the tube extending no farther from the center line of the tube than the distance from the center line of the tube to the drive gear when the instrument holder is inserted in the handpiece for operation.

6. The structure of claim 1 wherein the dental instrument has a conventional flat, the instrument holder comprises a tube, including a gear unitary with the tube, the means to rotate the dental instrument comprising a first inward projection unitary with the tube at a location above the gear, and the means to prevent the removal of the instrument while the instrument holder and the instrument are in motion comprises a second inward projection unitary with the tube at a location above the gear.

7. The structure of claim 1 wherein the latch means unitary with the tube releasable holding means includes a tube portion with latch means formed from and as an integral part of the tube portion of the instrument holder.

8. The structure of claim 7 wherein the latch means includes a latch arm formed by slots in the tube of the instrument holder, and having a projection extending inwardly from the arm formed between the slots, with the projection adapted to be engaged by a dental instrument.

9. The structure of claim 1, wherein the instrument holder means to prevent the removal of the instrument while the instrument holder and instrument are in motion includes a tube with a projection which is unitary with the tube extending inwardly from the wall of the tube and adapted to engage a instrument shank in a manner to prevent its removal.

10. The structure of claim 1 wherein the instrument holder means to prevent the removal of the dental instrument from the instrument holder while the instrument holder and instrument are in motion includes a tube with a projection which is unitary with the tube, extending inwardly from the wall of the tube and with the projection adapted to interact with a dental instrument of the type having a recessed surface in the top portion of its shank, and having a groove between the two ends of the vertical recession, so that there is a head at the top of the instrument shank, so that the interaction is such that the projection engages the instrument in the groove below the head when the instrument holder is rotated a predetermined distance around the dental instrument so that the projection rotates into the groove and prevents removal of the instrument from the instrument holder by exerting a resistant force against the head of the instrument shank.

11. In a dental handpiece for use in rotating an elongated dental tool that has a driven surface engageable to rotate it, and that has a transverse overhang; the handpiece having a bur tube with means thereon to engage the driven surface of the tool and means to underlie the overhang; the means to engage the driven surface having fixed angular relation to the means to underlie the overhang, that angular relation being such that when the tool and handpiece are relatively rotated, the drive means will not engage the driven surface until the means to underlie the overhang has fitted under the same, whereby during drive of the tool it cannot be withdrawn from the handpiece.

12. The handpiece of claim 11 wherein the means to engage the driven surface and the means to underlie the overhang are both fixed parts of the bur tube.

13. The handpiece of claim 11 wherein the means to engage the driven surface the means to underlie the overhang are separate means on the bur tube.

14. In a dental handpiece; an instrument holder comprising a tube with a unitary driven gear, releasable holding means to secure a dental instrument having a conventional flat in the instrument holder to prevent the instrument's removal but releasable to allow removal by a pull of the fingers comprising a latch arm formed by slots in the tube of the instrument holder, means to rotate the dental instrument with the instrument holder comprising a first inward projection unitary with the tube adapted to engage the flat of the dental instrument, means to prevent the removal of the instrument while the instrument holder and the instrument are in motion comprising a second inward projection unitary with the tube, and means to limit the outward displacement of the latch arm comprising a bearing sleeve which contacts the upper end of the tube.

15. In a dental handpiece: an instrument holder comprising a tube with a unitary gear, means to rotate a dental instrument having a conventional flat with the instrument holder comprising a first inward projection unitary with the tube adapted to engage the flat of the instrument, means to prevent the removal of the instrument while the instrument and instrument holder are in motion comprising a second inward projection unitary with the tube, and removable means for holding the instrument holder in the handpiece, comprising a single unit cap at the bottom of the handpiece whereby removal of the cap permits removal of the instrument holder from the handpiece.

16. In a dental handpiece using a dental instrument having a conventional flat and a transverse overhang, an instrument holder including a tube, releasable holding means to retain the instrument in the tube, but being releasable to allow removal of the instrument by a pull of the fingers, the holding means including a latch arm unitary with the tube; means to rotate the dental instrument with the instrument holder including an inward projection unitary with the tube adapted to engage the flat of the instrument; the instrument holder having means to prevent removal of the instrument while the instrument holder and instrument are in motion including an inward projection unitary with the tube adapted to engage the instrument shank beneath the overhang to prevent the instrument's removal.

17. In a dental handpiece, an instrument holder including a tube, means adapted to rotate a dental instrument having a cylindrical shank section and a conventional flat comprising a first inward projection unitary with the tube adapted to engage the flat of the dental instrument, and with means to prevent the removal of the instrument while the instrument holder and the instrument are in motion including a second inward projection unitary with the tube adapted to engage the instrument shank in a manner to prevent its removal, the tube having means to guide the rotation of the dental instrument including a cylindrical bore adapted to telescopically receive a portion of the cylindrical shank of the instrument, and a cylindrical exterior adapted to be received in a cylindrical bore.

18. In a dental handpiece, an instrument holder including a tube, with means to rotate a dental instrument having a cylindrical shank section and a conventional flat comprising a first inward projection unitary with the tube adapted to engage the flat of the dental instrument, and with means to prevent the removal of the instrument while the instrument holder and instrument are in motion including a second inward projection unitary with the tube adapted to engage the instrument shank in a manner to prevent its removal, and with means to guide the rotation of the instrument including a cap adapted to be attached to the bottom of the handpiece, and having a bore which receives a portion of the cylindrical shank of the instrument.

* * * * *

UNITED STATES PATENT OFFICE
CERTIFICATE OF CORRECTION

PATENT NO. : 4,014,099
DATED : March 29, 1977
INVENTOR(S) : Bailey, Ronald L.

It is certified that error appears in the above-identified patent and that said Letters Patent are hereby corrected as shown below:

Claim 1, line 46, "hollow" should read -holder-;

Claim 1, line 50, "aperature" should read -operative-.

Claim 7 (original claim 3, twice amended) should read as follows:

"7. The structure of claim 1 wherein the releasable holding means includes a tube portion with latch means unitary with the tube."

Signed and Sealed this second Day of August 1977

[SEAL]

Attest:

RUTH C. MASON
Attesting Officer

C. MARSHALL DANN
Commissioner of Patents and Trademarks